United States Patent
Colle et al.

(10) Patent No.: US 10,455,847 B2
(45) Date of Patent: Oct. 29, 2019

(54) CONFECTIONARY PRODUCTS WITH CALCIUM PHOSPHATE

(71) Applicant: PERFETTI VAN MELLE S.P.A., Lainate (Mi) (IT)

(72) Inventors: Roberto Colle, Lainate (IT); Andrea Sarrica, Lainate (IT)

(73) Assignee: Perfetti Van Melle S.p.A., Lainate (Milan) (IT)

( * ) Notice: Subject to any disclaimer, the term of this patent is extended or adjusted under 35 U.S.C. 154(b) by 0 days.

(21) Appl. No.: 15/039,422

(22) PCT Filed: Nov. 27, 2014

(86) PCT No.: PCT/EP2014/075769
§ 371 (c)(1),
(2) Date: May 26, 2016

(87) PCT Pub. No.: WO2015/078950
PCT Pub. Date: Jun. 4, 2015

(65) Prior Publication Data
US 2016/0374363 A1    Dec. 29, 2016

(30) Foreign Application Priority Data
Nov. 29, 2013    (IT) .............. MI2013A2003

(51) Int. Cl.
| | |
|---|---|
| *A23G 4/08* | (2006.01) |
| *A61K 8/24* | (2006.01) |
| *A23G 4/06* | (2006.01) |
| *A23G 3/00* | (2006.01) |
| *A23G 3/36* | (2006.01) |
| *A23G 3/54* | (2006.01) |
| *A61K 8/60* | (2006.01) |
| *A61Q 11/00* | (2006.01) |
| *A23G 4/20* | (2006.01) |
| *A61K 8/02* | (2006.01) |
| *A61K 8/21* | (2006.01) |

(52) U.S. Cl.
CPC ............. *A23G 4/064* (2013.01); *A23G 3/362* (2013.01); *A23G 3/54* (2013.01); *A23G 4/06* (2013.01); *A23G 4/062* (2013.01); *A23G 4/20* (2013.01); *A61K 8/0204* (2013.01); *A61K 8/21* (2013.01); *A61K 8/24* (2013.01); *A61K 8/60* (2013.01); *A61Q 11/00* (2013.01); *A23V 2002/00* (2013.01); *A61K 2800/30* (2013.01)

(58) Field of Classification Search
CPC ........ A23G 4/064; A23G 3/362; A23G 4/062; A23G 3/54; A23G 4/06; A23G 4/20; A61K 8/24; A61K 8/0204; A61K 8/21; A61K 8/60; A61K 2800/30; A61K 33/06; A61Q 11/00; A23V 2002/00
See application file for complete search history.

(56) References Cited

U.S. PATENT DOCUMENTS

| | | | | |
|---|---|---|---|---|
| 4,612,053 A | * | 9/1986 | Brown ..................... | A61K 8/24 106/35 |
| 2001/0051136 A1 | * | 12/2001 | Winston .................. | A61K 8/19 424/49 |
| 2005/0069608 A1 | | 3/2005 | Hendricks | |
| 2007/0183984 A1 | | 8/2007 | Haas et al. | |

FOREIGN PATENT DOCUMENTS

| | | |
|---|---|---|
| WO | 1998007448 A1 | 2/1998 |
| WO | 2000078270 A1 | 12/2000 |

OTHER PUBLICATIONS

Search Report and Written Opinion of PCT/EP2014/075769 dated Feb. 19, 2015.

* cited by examiner

*Primary Examiner* — Lezah Roberts
(74) *Attorney, Agent, or Firm* — Silvia Salvadori, P.C.; Silvia Salvadori

(57) ABSTRACT

The present invention relates to confectionary products containing a synergic combination of dibasic calcium phosphate and tribasic calcium phosphate. Confectionary products are useful in the treatment of dentinal sensitivity.

16 Claims, No Drawings

CONFECTIONARY PRODUCTS WITH CALCIUM PHOSPHATE

This application is a U.S. national stage of PCT/EP2014/075769 filed on 27 Nov. 2014, which claims priority to and the benefit of Italian Application No. MI2013A002003 filed on 29 Nov. 2013, the contents of which are incorporated herein by reference in their entireties.

SUMMARY OF THE INVENTION

The present invention relates to confectionary products which are useful in the treatment of dentinal sensitivity.

PRIOR ART

Dentinal sensitivity or hypersensitivity can be described as a brief, acute pain that originates from exposed dentine as a result of various kinds of stimulus: thermal, tactile, osmotic or chemical (Cunha-Cruz et al., JADA, 2013; 144 (3):288-296). This is a very common disorder, with a prevalence ranging from 3.8% to 74% of the population, depending on the groups studied and the study methods. Various active agents have been proposed to combat dentinal hypersensitivity: strontium and potassium salts, aldehydes, oxalates, bioactive glass, and arginine. Said active agents are mainly formulated as toothpastes, but chewing gums have also been proposed as calcium supplements. For example, EP0263224 discloses chewing gums comprising mineral salts applied in a coating. Calcium salts, such as dibasic calcium phosphate, tribasic calcium phosphate and hydroxyapatite, can alternatively be used as abrasives in chewing gum (U.S. Pat. No. 5,900,230, WO2013072932). Their use as an abrasive agent obviously has the opposite purpose to the treatment/prevention of dentinal sensitivity.

Calcium salts, in particular calcium carbonate, have been proposed in combination with guanidinium salts, such as arginine-bicarbonate, for the formulation of anti-dentinal hypersensitivity chewing gums (EP 1187593). Alternatively, calcium salts with a particle size of less than 50 µm have been formulated in acid chewing gums to act against dentinal sensitivity, tooth decay and demineralisation (WO9807448). However, the presence of acids is unsuitable for the treatment of dentinal sensitivity.

The prior art therefore treats calcium salts as an undifferentiated group, without identifying preferred salts and the corresponding doses, and uses acids because, by reducing the pH, they dissociate the calcium and phosphorus salts into their ions, thus promoting their dissolution.

A particular tribasic calcium phosphate is hydroxyapatite. This mineral forms part of the composition of enamel and dentine, constituting the majority thereof. For that reason, when administered in a suitable carrier, it is deposited "as is" on the tooth surfaces, and integrates with the underlying tissue. Calcium orthophosphate is similar to hydroxyapatite.

Some formulations use this particular salt in very small dimensions. IT RM93A000739 and EP1023035 disclose chewing gums for use in the treatment of hypersensitivity which comprise hydroxyapatite with a particle size ranging between 0.0001 and 1 µm. WO 00/03747, WO 2007/137606, EP2143415 and EP2077727 disclose the use of hydroxyapatites which are modified by substitution with carbonate, fluorine or other cations, or amorphised, and have nanometric dimensions.

However, these particular types of hydroxyapatite are not normally immediately available, but must be specifically prepared.

The prior art as a whole does not describe acid-free chewing gums containing synergic quantities of specific calcium salts for use in the treatment of dentinal sensitivity. The known use of tribasic calcium phosphate and dibasic calcium phosphate as abrasives clearly conflicts with the treatment of dentinal sensitivity. The presence of acids, as stated, is also undesirable, because it represents one of the stimuli that trigger the sensation of discomfort or pain in patients suffering from dentinal hypersensitivity.

Moreover, acid foods facilitate the dissolution of the enamel that protects the dentine and help to keep the dentinal tubules open, thus promoting the onset of sensitivity (Shiau, J Evid Base Dent Pract, 2012; S1:220-228) or increasing it where already present.

DESCRIPTION OF THE INVENTION

It has now been found that an acid-free confectionary product comprising 0.7% to 18% by weight of dibasic calcium phosphate and 0.07% to 3.6% by weight of tribasic calcium phosphate is useful and advantageous in the treatment of dentinal sensitivity.

The confectionary products according to the invention are candies, chewing gums and tablets, preferably chewing gums and tablets.

The products which can be used are either sugar-based or sugar-free, but the latter are preferred because they are not harmful to the dental tissues, including enamel and dentine.

The terms dentinal or dental sensitivity and hypersensitivity are used interchangeably herein.

The tribasic calcium phosphate is preferably selected from calcium orthophosphate and hydroxyapatite or mixtures thereof. Even more preferably, the tribasic calcium phosphate is hydroxyapatite.

Tribasic calcium phosphate has the characteristic of dispersing very easily in water, but in order to perform its mechanical and topical function effectively, and therefore to be deposited on the tooth surfaces and integrate with the underlying tissue, it must be scarcely soluble or insoluble. As known (JECFA, Tricalcium Phosphate, Prepared at the 17th JECFA (1973)), tribasic calcium phosphate is substantially insoluble in water at a neutral pH. Moreover, the simultaneous presence of a further, more soluble calcium salt, such as dibasic calcium phosphate, would contribute to saturating the environment, thus ensuring that the tribasic calcium phosphate does not dissolve.

Dibasic calcium phosphate can be used either as anhydrous dibasic calcium phosphate ($CaHPO_4$) or as dibasic calcium phosphate dihydrate ($CaHPO_4.2H_2O$). Mixtures thereof can optionally be used.

It is preferable for the dibasic calcium phosphate to be characterised in that at least 30% of the particles have a size exceeding 50 µm and 100% of the particles have a size of less than 150 µm.

The particle size indicated prevents the typical sandy or chalky sensations perceived when consuming food products containing calcium salts.

The invention therefore provides an adequate intake of tribasic calcium phosphate and prevents it from dissolving, thus allowing it to be deposited on the tooth surface and bond to it.

The confectionary product is preferably constituted by a chewing gum consisting of a plurality of regions and, in particular, of at least one first region with gum base and at least one completely water-soluble second region, without gum base. The dibasic calcium phosphate is preferably contained in the first region with gum base. Its inclusion in the region with gum base ensures gradual release of the ingredient during chewing, and a more effective saturation of plaque and oral fluids with calcium phosphate. In this way the tribasic calcium phosphate in the region not containing gum base, consisting of very small crystals, is protected against dissolution.

Preferably, 100% of the tribasic calcium phosphate particles have a size ranging between 0.10 µm and 60 µm. Alternatively, at least 90% of the particles of said tribasic calcium phosphate have a size of less than 0.3 µm. The use of tribasic calcium phosphate wherein at least 90% of the particles have a size of less than 0.010 µm is particularly preferred.

A smaller crystal size facilitates the deposit of tribasic calcium phosphate on or in the dentinal tubules, giving rise to their occlusion, and thus leading to a reduction in dentinal sensitivity.

A confectionary product that contains 3% to 10% by weight of dibasic calcium phosphate and 0.1% to 1% by weight of tribasic calcium phosphate is preferable.

A single piece of confectionary product preferably contains 10 mg to 250 mg of dibasic calcium phosphate, more preferably 40 mg to 140 mg, and 1 mg to 50 mg of tribasic calcium phosphate, even more preferably 1.4 mg to 14 mg.

A single piece of chewing gum can advantageously weigh 1 g to 3.5 g, preferably 1.2 g to 2.5 g, including mean weights of 1.4 g, 1.5 g, 1.7 g, 2 g, 2.2 g, 2.4 g.

A single tablet can advantageously weigh 0.1 g to 2 g, preferably 0.5 g to 1.5 g, including mean weights of 0.6 g, 0.7 g, 0.8 g, 1 g.

A final weight of a confectionary product within the values described provides a daily intake of a number of pieces and calories compatible with a balanced diet and normal lifestyle which, together with the specified doses, make its use effective in the treatment of dentinal sensitivity.

For use in the treatment of dentinal sensitivity, consumers should therefore preferably be advised to take 2 to 10 pieces of confectionary product a day. An amount of 4 to 8 pieces, taken after meals and snacks, is particularly preferred. The products according to the invention act most effectively in the treatment of dentinal sensitivity when taken at least three times a day, after breakfast, lunch and dinner, two pieces at a time, with a chewing or consumption time of 10 minutes.

The confectionary product according to the invention can also contain fluoride in amounts ranging from 0.001% to 0.15%, preferably 0.05% to 0.15%. The fluoride preferably takes the form of a soluble salt selected from sodium fluoride, sodium monofluorophosphate, ammonium fluoride and potassium fluoride and combinations thereof.

The preferred confectionary products are chewing gums.

Chewing gum is particularly advantageous for use in the treatment of dentinal sensitivity because chewing stimulates salivary secretion, leading to neutralisation of the acids in plaque which are generated when food residues are fermented by the oral flora. The stimulated saliva also produces further calcium and phosphorus salts.

The use of a carrier that neutralises any acids and stimulates the natural calcium and phosphorus intake is therefore also advantageous in the ambit of the invention, the formulation of which does not use acids.

A chewing gum dragée is particularly preferred. This is a gum comprising a first region with gum base, called the core, containing dibasic calcium phosphate, and a second, completely water-soluble region, without gum base, called the coating, which at least partly covers the first region and contains tribasic calcium phosphate. Chewing gum dragées can be made in different shapes, such as cushion, cubic or round shapes, etc.

The chewing gum according to the invention is preferably sugar-free, and more than 60% by dry weight of the coating consists of a polyol selected from xylitol, sorbitol, maltitol, mannitol, erythritol, glucopyranosyl-mannitol, glucopyranosyl-sorbitol and mixtures thereof.

The chewing gum according to the invention can also contain a filling in said core.

Alternatively, the confectionary product consists of chewing gum comprising a first region with gum base, containing dibasic calcium phosphate, and a second, completely water-soluble region, without gum base, containing tribasic calcium phosphate, configured as regions in the form of alternating layers.

The chewing gum can contain numerous ingredients and additives, such as gum base, sugars or sugar substitutes, sweeteners, intensive sweeteners, flavourings and dyes. Examples of chewing gum compositions and the methods of obtaining them are known and available in reference books (Sugar Confectionery Manufacture, 2nd ed., E.B Jackson, Aspen Publishers, Inc., Gaithersburg, Md. (1999)).

Alternatively, the product according to the invention can take the form of tablets or candies.

The tablets can be obtained by various techniques, and can have a hard or chewable texture. Dragée forms of tablets are also available. Unlike chewing gum, all regions of a tablet are water-soluble.

For financial reasons, it is preferable for the confectionary product according to the invention to consist of a simple tablet, preferably obtained by direct compression, containing an amount of dibasic calcium phosphate exceeding 0.01% and an amount of tribasic calcium phosphate exceeding 0.01% (percentages by weight of the finished product).

Alternatively, the tablets can also be in form of dragées. In such case the dibasic calcium phosphate is preferably present in the inner region, which consists of the tablet properly so called, while the tribasic calcium phosphate is preferably present in the outer coating region.

The preparation of the tablets is described, for example, in Sugar Confectionery Manufacture, 2nd ed., E.B Jackson, Aspen Publishers, Inc., Gaithersburg, Md. (1999).

The chewing gum can also take the form of a tablet comprising a totally soluble region overlaid on the region containing gum base, procured in powder form suitable to be processed by tablet-making machines, as reported in EP1427292. Once again it is preferable for the dibasic calcium phosphate to be contained in the region with gum base, while the tribasic calcium phosphate is contained in the completely water-soluble region.

Alternatively, the product according to the invention can take the form of candies such as hard candies, chewable or soft candies, gumdrops or lollipops.

Combinations between said forms, and between them and other ingredients, such as fillings and coatings, are possible.

A preferred embodiment of the invention consists of a chewable candy.

Soft dragées are also possible. In such case the dibasic calcium phosphate is preferably present in the inner region, which consists of the chewable candy properly so called, while the tribasic calcium phosphate is preferably present in the outer coating region.

In an even more preferred embodiment, the inner region in turn consists of two regions with different chewability characteristics.

The invention has been described in relation to its use in the treatment of dentinal sensitivity, but it can also be usefully applied for other purposes. In particular, the confectionary product according to the invention can be used in the treatment of demineralisation of tooth enamel and dentine, and in the treatment and prevention of tooth decay. Said uses are characterised by the need to provide the missing mineral fractions on the hard tissues of the tooth, and the dibasic calcium phosphate and tribasic calcium phosphate released by the confectionary product according to the invention fulfil this purpose.

EXAMPLES

Examples 1-4 Chewing Gum

Examples 1-4, shown in Table 1, illustrate chewing gum dragées made by conventional methods. The final weight of a piece is 1.4 g.

TABLE 1

| Ingredient | Example 1 (comparison) % | Example 2 (comparison) % | Example 3 (comparison) % | Example 4 (invention) % |
| --- | --- | --- | --- | --- |
| Core | | | | |
| Gum base | 26 | 26 | 26 | 26 |
| Maltitol syrup | 1 | 1 | 1 | 1 |
| Sorbitol | 30 | 26 | 30 | 26 |
| Aspartame | 0.3 | 0.3 | 0.3 | 0.3 |
| Acesulfame | 0.1 | 0.1 | 0.1 | 0.1 |
| Sucralose | 0.1 | 0.1 | 0.1 | 0.1 |
| Glycerin | 1 | 1 | 1 | 1 |
| Mannitol | 5 | 4 | 5 | 4 |
| Xylitol | 5 | 4 | 5 | 4 |
| Mint flavouring | 1.5 | 1.5 | 1.5 | 1.5 |
| Dibasic calcium phosphate | 0 | 6 | 0 | 6 |
| Coating | | | | |
| Xylitol | 22 | 21 | 21 | 21 |
| Mannitol | 5 | 5 | 5 | 5 |
| Gum arabic | 1.5 | 1.5 | 1.5 | 1.5 |
| Titanium dioxide | 0.7 | 0.7 | 0.7 | 0.7 |
| Aspartame | 0.1 | 0.1 | 0.1 | 0.1 |
| Sucralose | 0.1 | 0.1 | 0.1 | 0.1 |
| Mint flavouring | 0.4 | 0.4 | 0.4 | 0.4 |
| Powdered flavouring | 0.15 | 0.15 | 0.15 | 0.15 |
| Carnauba wax | 0.05 | 0.05 | 0.05 | 0.05 |
| Hydroxyapatite $0.1 < d100 < 50\ \mu m$ | 0 | 0 | 1 | 1 |
| Total | 100 | 100 | 100 | 100 |

Example 5—Test

A group of 18 healthy volunteers was recruited according to the following criteria: surface hypersensitivity of two or more teeth with a response of at least one on the ice test scale, good periodontal state (no pockets exceeding 4 mm), no pathological condition that could explain the apparent hypersensitivity, age between 18 and 55 years, good general state of health, willingness to attend appointments and take part in the study, and signature of a written consent form. Exclusion criteria were also established.

The volunteers were divided into three groups of equal numbers, and one of the chewing gums described in examples 2, 3, 4 was assigned to each group.

Group A→Example 2 (comparison)
Group B→Example 3 (comparison)
Group C→Example 4 (invention)

The volunteers were instructed to chew two gums together after breakfast, lunch and dinner Dentinal sensitivity was measured before the start of the treatment period and after one, two and four weeks.

Sensitivity was determined by the methods reported in the literature, (Orsini et al J Clin Periodontol 2010; 37 (6):510-7) on the basis of four parameters: tactile sensitivity, sensitivity to cold air or cold water (measured by a dentist), and subjectively perceived sensitivity (reported by the volunteers).

Table 2 shows the percentage reduction in mean sensitivity compared with the starting conditions with the four stimuli.

TABLE 2

| | | % variation in sensitivity | | |
| --- | --- | --- | --- | --- |
| Group | Sensitivity stimulus | after 1 week | after 2 weeks | after 4 weeks |
| Group A (comparison) | tactile | −8 | −18 | −26 |
| | air | −3 | −15 | −20 |
| | water | −3 | −14 | −18 |
| | subjective | −12 | −21 | −28 |
| Group B (comparison) | tactile | −9 | −11 | −9 |
| | air | −6 | −13 | −15 |
| | water | −7 | −7 | −10 |
| | subjective | −3 | −5 | −6 |
| Group C (invention) | tactile | −33 | −56 | −56 |
| | air | −8 | −33 | −58 |
| | water | −25 | −31 | −31 |
| | subjective | −19 | −38 | −68 |

Groups A, B, C showed a reduction in sensitivity compared with the starting conditions, which increased over the treatment period. However, the data for Group C showed an improvement greater than the sum of those for Groups B and C, indicating that the ingredients according to the invention have a synergic effect. Table 3 shows the percentage synergic effect for each stimulus after 1, 2 and 4 weeks, obtained by subtracting the sum of the variations relating to groups A and B from the % variation in sensitivity for Group C, and dividing the total by the % variation in sensitivity of Group C multiplied by 100.

$$\% \text{ synergic effect} = 100 * ((VS\ \%_C - (VS\ \%_A + VS\ \%_B))/VS\ \%_C$$

VS % = % variation in sensitivity

TABLE 3

| | % synergic effect | | |
| --- | --- | --- | --- |
| Sensitivity stimulus | after 1 week | after 2 weeks | after 4 weeks |
| tactile | 48.5 | 48.2 | 37.5 |
| air | −12.5 | 15.2 | 39.7 |
| water | 60.0 | 32.3 | 9.7 |
| subjective | 21.1 | 31.6 | 50.0 |
| mean | 29.3 | 31.8 | 34.2 |

The synergic effect was already detectable as from the first week in three tests out of 4, and in the second and fourth week in all four tests. The average synergic effect over the four tests is close to 30%, with a tendency to improve over time.

Example 6 (Invention)

A chewing gum was made with the same composition as described in example 4, except that 0.4% of hydroxyapatite, wherein over 90% of the particles had a diameter of less than 0.01 μm, was used.

Example 7 (Test)

The gums described in example 6 were tested on 4 volunteers (Group D), using the same protocol as in example 4 (Table 4).

TABLE 4

| Group | Sensitivity stimulus | % sensitivity after 2 weeks | after 4 weeks |
|---|---|---|---|
| Group D | tactile | −70 | −100 |
| | air | −50 | −70 |
| | water | −61 | −94 |
| | subjective | −64 | −86 |

Dentinal sensitivity decreased to a particularly evident extent when the gums described in example 6 were used, more markedly than in Group C.

Examples 8, 9—Tablets

The sugar-free tablets having the compositions illustrated in Table 5 were made by the direct compression method. The tablets weighed 0.7 g each.

TABLE 5

| Ingredient | Example 8 (invention) % | Example 9 (invention) % |
|---|---|---|
| Sorbitol | 92.3 | 81.3 |
| Xylitol | | 10 |
| Acesulfame K | 0.2 | 0.2 |
| Aspartame | 0.35 | 0.25 |
| Emulsifiers | 1 | 1 |
| Silicon dioxide | 1 | 1 |
| Mint flavouring | 2.45 | |
| Peach flavouring | | 1.85 |
| Dibasic calcium phosphate | 2 | 4 |
| Tribasic calcium phosphate | 0.7 | 0.4 |
| Total | 100 | 100 |

Example 10 (Test)

The tablets described in example 8 were tested on 5 volunteers (Table 6, Group E) using the same protocol as in example 4, to test subjective sensitivity.

TABLE 6

| Group | Sensitivity stimulus | % sensitivity after 1 weeks | after 2 weeks |
|---|---|---|---|
| Group E | subjective | −16 | −22 |

The invention claimed is:

1. A method of treating dentinal sensitivity in a subject in need thereof, said method comprising:
   administering to said subject a confectionary product free from acids and comprising calcium phosphate, wherein said calcium phosphate consists of from 0.7% to 18% by weight of dibasic calcium phosphate and from 0.07% to 3.6% by weight of tribasic calcium phosphate.

2. The method according to claim 1 wherein dibasic calcium phosphate is selected from anhydrous dibasic calcium phosphate, dibasic calcium phosphate dihydrate and mixtures thereof.

3. The method according to claim 1 wherein said dibasic calcium phosphate has at least 30% of the particles with a size larger than 50 μm.

4. The method according to claim 1 wherein tribasic calcium phosphate is selected from calcium orthophosphate, calcium hydroxyapatite and mixtures thereof.

5. The method according to claim 1 wherein said tribasic calcium phosphate has 100% of the particles with a size ranging from 0.10 μm to 60 μm.

6. The method according to claim 1 wherein said tribasic calcium phosphate has at least 90% of the particles with a size of less than 0.3 μm.

7. The method according to claim 6 wherein said tribasic calcium phosphate has at least 90% of the particles with a size of less than 0.010 μm.

8. The method according to claim 1, wherein in a single piece, dibasic calcium phosphate is present in amounts ranging from 10 mg to 250 mg and tribasic calcium phosphate is present in amounts ranging from 1 mg to 50 mg.

9. The method according to claim 1 containing fluoride in amounts ranging from 0.001% to 0.1%.

10. The method according to claim 1, said confectionary product consists of a chewing gum dragee, comprising:
    i) a first region comprising a gum base as a core and said dibasic calcium phosphate; and
    ii) a second region that is a water-soluble coating layer, which comprises said tribasic calcium phosphate and no gum base, wherein said tribasic calcium phosphate comprises more than 60% of the dry weight of the coating layer;
    wherein said second region at least partially coats said first region i).

11. The method according to claim 10, wherein the coating layer of the chewing gum dragee comprises a polyol selected from the group consisting of xylitol, sorbitol, maltitol, mannitol, erythritol, glucopyranosyl-mannitol, glucopyranosyl-sorbitol and mixtures thereof; wherein the polyol comprises more than 60% of the dry weight of the coating layer.

12. The method according to claim 1, said confectionary product is a chewing gum comprising:
    i) a first region comprising a gum base and said dibasic calcium phosphate; and ii) a second region comprising said tribasic calcium phosphate and no gum base; wherein the second region is water soluble;
    wherein the first region i) and the second region ii) are layered, mutually alternating regions.

13. A method of treating and preventing dentine and enamel demineralization in a subject in need thereof, said method comprising:
    administering to said subject a confectionary product free from acids and comprising calcium phosphate, wherein said calcium phosphate consists of from 0.7% to 18% by weight of dibasic calcium phosphate and from 0.07% to 3.6% by weight of tribasic calcium phosphate.

14. A method of treating and preventing dental caries in a subject in need thereof, said method comprising:
administering to said subject a confectionary product free from acids and comprising calcium phosphate, wherein said calcium phosphate consists of from 0.7% to 18% by weight of dibasic calcium phosphate and from 0.07% to 3.6% by weight of tribasic calcium phosphate.

15. The method according to claim 1 comprising administration of 2 to 10 pieces daily of said confectionary product.

16. The method according to claim 1, wherein said confectionary product is selected from the group consisting of candies, chewing gum and tablets.

* * * * *